US010682360B2

(12) United States Patent
Gardner

(10) Patent No.: US 10,682,360 B2
(45) Date of Patent: Jun. 16, 2020

(54) ANTIMICROBIAL FORMULATIONS AND APPLICATIONS THEREOF

(71) Applicant: Susanne Gardner, Atlanta, GA (US)

(72) Inventor: Susanne Gardner, Atlanta, GA (US)

( * ) Notice: Subject to any disclaimer, the term of this patent is extended or adjusted under 35 U.S.C. 154(b) by 344 days.

(21) Appl. No.: 15/114,208

(22) PCT Filed: Jan. 26, 2015

(86) PCT No.: PCT/US2015/012899
§ 371 (c)(1),
(2) Date: Jul. 26, 2016

(87) PCT Pub. No.: WO2015/112977
PCT Pub. Date: Jul. 30, 2015

(65) Prior Publication Data
US 2017/0007616 A1    Jan. 12, 2017

Related U.S. Application Data

(60) Provisional application No. 61/932,048, filed on Jan. 27, 2014.

(51) Int. Cl.
*A61K 31/546* (2006.01)
*A61K 45/06* (2006.01)
*A61K 31/545* (2006.01)
*A61K 38/12* (2006.01)
*A61K 31/5383* (2006.01)
*A61K 31/7036* (2006.01)
*A61K 38/13* (2006.01)
*A61K 9/00* (2006.01)

(52) U.S. Cl.
CPC ........ *A61K 31/546* (2013.01); *A61K 31/5383* (2013.01); *A61K 31/545* (2013.01); *A61K 31/7036* (2013.01); *A61K 38/12* (2013.01); *A61K 38/13* (2013.01); *A61K 45/06* (2013.01); *A61K 9/0019* (2013.01); *A61K 9/0048* (2013.01)

(58) Field of Classification Search
CPC .............. A61K 31/545; A61K 31/7036; A61K 31/473; A61K 31/496; A61K 38/12
See application file for complete search history.

(56) References Cited

U.S. PATENT DOCUMENTS

| | | |
|---|---|---|
| 5,169,637 A | 12/1992 | Lenk et al. |
| 7,671,070 B2 * | 3/2010 | Cagle ................... A61K 9/0043 514/314 |
| 2003/0176327 A1 | 9/2003 | Cassell et al. |
| 2007/0054844 A1 | 3/2007 | Lane et al. |
| 2010/0233241 A1 | 9/2010 | Leahy et al. |
| 2014/0039386 A1 | 2/2014 | Schafer |

FOREIGN PATENT DOCUMENTS

| | | |
|---|---|---|
| CN | 1543958 | 11/2004 |
| FR | 2448903 | 2/1979 |
| GB | 1400464 | 7/1975 |
| RU | 123655 | 1/2013 |
| WO | 2010103119 | 9/2010 |
| WO | 2017019943 | 2/2017 |

OTHER PUBLICATIONS

Zhanel et al. J. Antimicrob. Chemother., 2013, vol. 68, Suppl. 1, pp. i7-i22 (Year: 2013).*
Rhee et al. Am. J. Opthalmol., 2004, vol. 138, pp. 226-230 (Year: 2004).*
Schaefer et al. Br. J. Ophthalmol., 2001, vol. 85, pp. 842-847 (Year: 2001).*
Sueke et al. Invest. Ophthalmol., 2010, vol. 51, pp. 2519-2524 (Year: 2010).*
Sharma et al. Optom. Vis. Sci., 2013, vol. 90, No. 2, pp. e53-e55 (Abstract Attached) (Year: 2013).*
International Search Report and Written Opinion for PCT/US15/12899 dated May 11, 2015.
International Search Report and Written Opinion for PCT/US16/44661 dated Oct. 17, 2016.
Elemam et al., In vitro evaluation of antiobiotic synergy for polymyxin B-resistant carbapenemase-producing Klebsiella pneumoniae, 2010, J. Clin. Microbial., 48:3558-3562.
Freling et al., Differential induction of pro- and anti-inflammatory cytokines in whole blood by bacteria: effects of antibiotic treatment, 1997, Antimicrob. Agents & Chemother., 41:1439-1443.
Halder et al., Comparative evaluation of aqueous and plasma concentration of topical moxifloxacin alone and with flurbiprofen in patients of cataract surgery, 2013, Indian J. Pharmacol., 45:223-226.
Lim et al., Effective antibiotics in combination against extreme drug-resistant Pseudomonas aeruginosa with decreased susceptibility to polymyxin B, 2011, PLOS One, 6:e28177.

(Continued)

*Primary Examiner* — James D. Anderson
(74) *Attorney, Agent, or Firm* — Thomas|Horstemeyer, LLP

(57) ABSTRACT

Described herein are new approaches to antimicrobial therapy, which includes the development of new combinations of antibiotic agents as well as their use for specific therapeutic purposes. These specific therapeutic purposes may apply to clinical situations inherently different from treatment of infections that require systemic antibiotic administration. More localized approaches offer a number of advantages. The advantages of such antibiotic combinations include, but are not limited to, targeting a broader spectrum of microbes; faster microbial eradication; sparing the subject systemic exposure to the individual antimicrobial agents; enhancing the antimicrobial activity against microbes considered resistant to individual agents; and enhancing the antimicrobial activity against microbes considered resistant to individual agents at levels appropriate for systemic administration.

24 Claims, No Drawings

(56) References Cited

OTHER PUBLICATIONS

Nakai et al., Incompatibility of ceftriaxone sodium with calcium-containing products, 2009, Yakugaku Zasshi, 129:1385-1392.
Schaefer et al., Acutite otitis externa: an update, 2012, American Family Physician, 86:1055-1061.

\* cited by examiner

ANTIMICROBIAL FORMULATIONS AND APPLICATIONS THEREOF

CROSS REFERENCE TO RELATED APPLICATION

This application claims priority upon U.S. Provisional Application Ser. No. 61/932,048, filed Jan. 27, 2014. This application is hereby incorporated by reference in its entirety for all of its teachings.

BACKGROUND

Standard assessments of antibiotic antimicrobial effects are generally centered around antibiotic concentrations that are safely achievable in serum, reflecting scenarios of multiple systemically delivered doses over time. Clinical situations where altogether different scenarios prevail are fewer in number and may represent "orphan" areas of clinical needs. Little to no data are available for antibiotics/combinations utilized and delivered in categorically atypical concentrations or methods for localized needs, or non-systemic needs. In addition, the microbial composition of localized infections warrants new approaches to local delivery of antibiotics or antibiotic combinations, where issues of local vs. systemic toxicity are separated, and where additive, potentiating or synergistic actions of the antimicrobials are explored for specific clinical needs. For example, such a clinical need is exemplified by intraocular or periocular injections that take into account the unique pharmacokinetic/pharmacodynamic (PK/PD) aspects of the eye, and its surrounding tissues. These interventions may represent prophylactic or treatment measures. Similar unique approaches apply to other localized infections or applications where unique PK/PD factors apply, but are not well served under current circumstances. No single antibiotic agent, or available compound, is currently indicated to eradicate both the highly pathogenic Gram-positive microbes (such as methicillin-resistant staphylococci) and Gram-negative microbes (such as *Pseudomonas aeruginosa*) encountered in certain circumstances, or eradicates these microbes in rapid, unique time frames that may be needed in organs such as the eye. The compositions and methods described herein offer sight-saving interventions and reductions in morbidity under specialized circumstances that are currently not served.

SUMMARY

Described herein are new approaches to antimicrobial therapy, which includes the development of new combinations of antibiotic agents as well as their use for specific therapeutic purposes. These specific therapeutic purposes may apply to clinical situations inherently different from treatment of infections that require systemic antibiotic administration. More localized approaches offer a number of advantages. The advantages of such antibiotic combinations include, but are not limited to, targeting a broader spectrum of microbes; faster microbial eradication; sparing the subject to systemic exposure of the individual antimicrobial agents; enhancing the antimicrobial activity against microbes considered resistant to individual agents; and enhancing the antimicrobial activity against microbes considered resistant to individual agents at levels appropriate for systemic administration. Further advantages and applications are described below.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "treat" as used herein is defined as maintaining or reducing the symptoms of a pre-existing condition when administered the antimicrobial agents described herein when compared to the same symptom in the subject prior to the administration of the antimicrobial agents to the subject.

The term "prevent" is defined herein as reducing or eliminating the growth rate of bacteria in a subject when administered the antimicrobial agents described herein when compared to the growth rate in the same subject prior to the administration of the antimicrobial agents to the subject. The term "prevent" is also defined as eliminating the onset of any bacterial growth in a subject, where no bacteria existed in the subject. The term "prevent" is also defined as eliminating the onset of one or more symptoms in a subject when administering the antimicrobial agents described herein when compared to the same symptom in the subject prior to the administration of the antimicrobial agents to the subject.

The term "subject" as defined herein is any organism that is in need of bacteria eradication or prevention of bacteria growth. In one aspect, the subject is a mammal including, but not limited to, humans, domesticated animals (e.g., dogs, cats, horses), livestock (e.g., cows, pigs), and wild animals.

Described herein are combinations of antimicrobial agents and their applications thereof. As discussed in detail below, the antimicrobial agents used herein are useful in rapidly killing bacteria in a subject. The nature of the antimicrobial agents, the modes of administration, applications, and the numerous advantages of the invention are described in detail below.

Antimicrobial Agents

The concentrations of antimicrobial agents described herein are considerably higher than serum levels achieved after systemic administration. In one aspect, at least one antimicrobial agent described herein has a concentration at least two multiples of customary serum concentrations achieved after systemic administration of that agent. In another aspect, at least one antimicrobial agent described herein has a concentration of two to three multiples, two to four multiples, or two to five multiples of customary serum concentrations achieved after systemic administration of that agent. The significance of the selection of the antimicrobial agents and their concentrations thereof is discussed in detail below.

In one aspect, the subject is administered (a) at least one cephalosporin and (b) at least one polymyxin. Examples of cephalosporins useful herein include, but are not limited to, cefazolin, cefuroxime, ceftazidime, cephalexin, cephaloridine, cefamandole, cefsulodin, cefonicid, cefoperazine, cefoprozil, ceftriaxone, or any combination thereof. In one aspect, the cephalosporin is cefazolin, cefuroxime, ceftazidime, or any combination thereof.

The concentration of the cephalosporin can vary depending upon the application. In one aspect, the cephalosporin has a concentration from 0.1 mcg/ml to 4,000 mcg/ml. In another aspect, the cephalosporin has a concentration of 10 mcg/ml to 4,000 mcg/ml, 100 mcg/ml to 4,000 mcg/ml, 250 mcg/ml to 4,000 mcg/ml, 500 mcg/ml to 4,000 mcg/ml, or 1,000 mcg/ml to 4,000 mcg/ml. In another aspect, the cephalosporin has a concentration from 0.001 mg/ml to 50 mg/ml, 0.01 mg/ml to 50 mg/ml, 0.1 mg/ml to 50 mg/ml, 0.2 mg/ml to 50 mg/ml, 1 mg/ml to 50 mg/ml, 2 mg/ml to 50 mg/ml, 5 mg/ml to 50 mg/ml, 5 mg/ml to 50 mg/ml, 5 mg/ml to 40 mg/ml, 5 mg/ml to 30 mg/ml, or 5 mg/ml to 20 mg/ml.

Examples of polymyxins useful herein include, but are not limited to, polymyxin B, colistin, or a combination thereof. In one aspect, the polymyxin has a concentration from, 0.0001 mcg/ml to 1,000 mcg/ml, 0.001 mcg/ml to 1,000 mcg/ml, 0.01 mcg/ml to 1,000 mcg/ml, 0.1 mcg/ml to 1,000 mcg/ml, 1 mcg/ml to 1,000 mcg/ml, 10 mcg/ml to 1,000 mcg/ml, 50 mcg/ml to 1,000 mcg/ml, or 100 mcg/ml to 1,000 mcg/ml. In another aspect, the polymyxin has a concentration from 0.0001 mg/ml to 5 mg/ml, 0.001 mg/ml to 5 mg/ml, 0.1 mg/ml to 5 mg/ml, or 0.5 mg/ml to 5 mg/ml.

In one aspect, the cephalosporin has a concentration of 0.001 mg/ml to 50 mg/ml, 0.01 mg/ml to 50 mg/ml, 0.1 mg/ml to 50 mg/ml, 0.2 mg/ml to 50 mg/ml, 1 mg/ml to 50 mg/ml, 2 mg/ml to 50 mg/ml, 5 mg/ml to 50 mg/ml, 5 mg/ml to 50 mg/ml, 5 mg/ml to 40 mg/ml, 5 mg/ml to 30 mg/ml, or 5 mg/ml to 20 mg/ml and the polymyxin has a concentration of 0.0001 mg/ml to 5 mg/ml.

In certain aspects, one or more additional antimicrobial agents can be administered to the subject in combination with the cephalosporin and polymyxin. In one aspect, the subject is further administered an aminoglycoside. Examples of aminoglycosides useful herein include, but are not limited to, gentamicin, amikacin, tobramycin, debekacin, kanamycin, neomycin, netilmicin, paromomycin, sisomycin, spectinomycin, streptomycin, or any combination thereof. In one aspect, the aminoglycoside has a concentration from 0.001 mcg/ml to 1,000 mcg/ml, 0.01 mcg/ml to 1,000 mcg/ml, 0.1 mcg/ml to 1,000 mcg/ml, 0.5 mcg/ml to 1,000 mcg/ml, 1 mcg/ml to 1,000 mcg/ml, 10 mcg/ml to 1,000 mcg/ml, 100 mcg/ml to 1,000 mcg/ml, 250 mcg/ml to 1,000 mcg/ml, 500 mcg/ml to 1,000 mcg/ml. In another aspect, the aminoglycoside has a concentration from 0.1 mg/ml to 20 mg/ml, 0.5 mg/ml to 20 mg/ml, or 1 mg/ml to 20 mg/ml.

In one aspect, the cephalosporin has a concentration of 0.001 mg/ml to 50 mg/ml, 0.01 mg/ml to 50 mg/ml, 0.1 mg/ml to 50 mg/ml, 0.2 mg/ml to 50 mg/ml, 1 mg/ml to 50 mg/ml, 2 mg/ml to 50 mg/ml, 5 mg/ml to 50 mg/ml, 5 mg/ml to 50 mg/ml, 5 mg/ml to 40 mg/ml, 5 mg/ml to 30 mg/ml, or 5 mg/ml to 20 mg/ml, the polymyxin has a concentration of 0.0001 mg/ml to 5 mg/ml, and the aminoglycoside has a concentration from 0.1 mg/ml to 20 mg/ml.

In another aspect, the subject is further administered a fluoroquinolone in combination with the cephalosporin, polymyxin, and optionally an aminoglycoside. Examples of fluoroquinolones useful herein include, but are not limited to, levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, besifloxacin, or any combination thereof. In one aspect, the fluoroquinolone has a concentration from 0.01 mcg/ml to 5,000 mcg/ml, 0.1 mcg/ml to 5,000 mcg/ml, 1 mcg/ml to 5,000 mcg/ml, 10 mcg/ml to 5,000 mcg/ml, 100 mcg/ml to 5,000 mcg/ml, 500 mcg/ml to 5,000 mcg/ml, or 1,000 mcg/ml to 5,000 mcg/ml. In another aspect, the fluoroquinolone has a concentration from 0.05 mg/ml to 20 mg/ml, 0.1 mg/ml to 20 mg/ml, 0.5 mg/ml to 20 mg/ml, 1 mg/ml to 20 mg/ml, 2 mg/ml to 20 mg/ml, 3 mg/ml to 20 mg/ml, 3 mg/ml to 15 mg/ml, or 3 mg/ml to 10 mg/ml.

In one aspect, the cephalosporin has a concentration of 0.001 mg/ml to 50 mg/ml, 0.01 mg/ml to 50 mg/ml, 0.1 mg/ml to 50 mg/ml, 0.2 mg/ml to 50 mg/ml, 1 mg/ml to 50 mg/ml, 2 mg/ml to 50 mg/ml, 5 mg/ml to 50 mg/ml, 5 mg/ml to 50 mg/ml, 5 mg/ml to 40 mg/ml, 5 mg/ml to 30 mg/ml, or 5 mg/ml to 20 mg/ml, the polymyxin has a concentration of 0.0001 mg/ml to 5 mg/ml, the aminoglycoside has a concentration from 0.1 mg/ml to 20 mg/ml, and the fluoroquinolone has a concentration from 0.05 mg/ml to 20 mg/ml.

In one aspect, the subject is administered (1) cefazolin and (2) polymyxin B, wherein the cefazolin is from 0.001 mg/ml to 20 mg/mL and the polymyxin B is from 0.0001 mg/ml to 5 mg/ml.

In another aspect, the subject is administered (1) cefazolin, (2) polymyxin B, and (3) amikacin, wherein the cefazolin is from 0.001 mg/ml to 20 mg/mL, the polymyxin B is from 0.001 mg/ml to 5 mg/ml, and the amikacin is from 0.001 mg/ml to 10 mg/ml.

In another aspect, the subject is administered (1) cefazolin, cefuroxime, ceftazidime or a combination thereof, (2) polymyxin B, (3) amikacin, and (4) levofloxacin, wherein the cefazolin is from 0.001 mg/ml to 20 mg/mL, the polymyxin B is from 0.001 mg/ml to 5 mg/ml, the amikacin is from 0.01 mg/ml to 10 mg/ml, and the levofloxacin is from 0.05 mg/ml to 10 mg/ml.

In another aspect, the subject is administered (1) cefuroxime and (2) polymyxin B, wherein the cefuroxime is from 0.01 mg/ml to 20 mg/mL and the polymyxin B is from 0.001 mg/ml to 5 mg/ml.

In another aspect, the subject is administered (1) cefuroxime, (2) polymyxin B, and (3) amikacin, wherein the cefuroxime is from 0.01 mg/ml to 20 mg/mL, the polymyxin B is from 0.001 mg/ml to 5 mg/ml, and the amikacin is from 0.001 mg/ml to 10 mg/ml.

In another aspect, the subject is administered (1) cefuroxime, (2) ceftazidime, and (3) polymyxin B, wherein the cefuroxime is from 0.01 mg/ml to 20 mg/mL, the ceftazidime is from 0.001 mg/ml to 10 mg/mL, and the polymyxin B is from 0.001 mg/ml to 5 mg/ml.

In another aspect, the subject is administered (1) cefuroxime, (2) ceftazidime, (3) polymyxin B, and (4) levofloxacin, wherein the cefuroxime is from 0.01 mg/ml to 20 mg/mL, the ceftazidime is from 0.001 mg/ml to 10 mg/mL, the polymyxin B is from 0.001 mg/ml to 5 mg/ml, and the levofloxacin is from 0.05 mg/ml to 10 mg/ml.

In another aspect, the subject is administered (1) cefuroxime, (2) ceftazidime, (3) polymyxin B, (4) levofloxacin, and (5) amikacin, wherein the cefuroxime is from 0.01 mg/ml to 20 mg/mL, the ceftazidime is from 0.001 mg/ml to 10 mg/mL, the polymyxin B is from 0.001 mg/ml to 5 mg/ml, the levofloxacin is from 0.05 mg/ml to 10 mg/ml, and the amikacin is from 0.001 mg/ml to 10 mg/ml.

In another aspect, the subject is administered (a) at least one cephalosporin and (b) at least one aminoglycoside. Any of the cephalosporins and aminoglycosides described above as well as the concentration ranges can be used in this aspect. In one aspect, the cephalosporin is cefuroxime and the aminoglycoside is amikacin, wherein the cefuroxime is from 0.01 mg/ml to 20 mg/mL and the amikacin is from 0.001 mg/ml to 10 mg/ml.

Depending upon the application, one or more additional biological agents can be administered with the antimicrobial agents. In one aspect, the subject is further administered corticosteroid agents and congeners including, but not limited to, betamethasone, dexamethasone, fludrocortisone, hydrocortisone, tixorcortol, prednisolone, methylprednisolone mometasone, amcinonide, budesonide, desonide, fluocinonide, halcinonide, fluocortolone, flunisolide, fluocortolone, fluticasone, fluprednidene, beclomethasone, budesonide, clobetasone, prednicarbate, fluticasone, or any combination thereof.

Applications and Modes of Administration

The antimicrobial agent combinations and concentrations used herein are effective in rapidly killing bacteria in a subject. In one aspect, upon administration of the antimicrobial agents, 10 to 100% of the bacteria in the subject are killed within 1 to 16 hours, 1 to 14 hours, 1 to 12 hours, 1 to 10 hours, 1 to 8 hours, 1 to 6, 1 to 4 hours, or 1 to 2 hours. In another aspect, 10 to 100%, 25 to 100%, 50 to 100%, 75 to 100%, or 95 to 100% of the bacteria in the subject are killed within 1 to 2 hours after administration of the antimicrobial agents.

The antimicrobial agents described herein are useful in clinical situations inherently different from treatment of infections that require systemic antibiotic administration. The antimicrobial agents used herein permit the localized administration of the agents to a specific site in the subject. There are numerous advantages to this approach including, but are not limited to: localized targeting of microbes; local use of antimicrobials that are associated with toxicity after systemic administration; avoidance of allergic reactions; sparing of antibiotics that are deemed critical for systemic use in the treatment of serious infections; use of antibiotic concentrations that reduce the propensity for microbial resistance development. Additionally, in certain aspects, the use of the antimicrobial agents at the concentrations and combinations described herein only require one or two dose applications where multiple applications are not practical. Moreover, the ability of the antimicrobial agents to rapidly kill bacteria or prevent the growth of bacteria reduces or prevents local tissue damage caused by replicating bacteria during an infection.

Additionally, the antimicrobial agent combinations and concentrations described herein permit the use of two or more antibiotics in combination, where the combination targets a broader spectrum of microbes; where the combination allows faster microbial eradication; where the combination spares systemic exposure to the individual antimicrobial agents; where the combination has antimicrobial activity against microbes considered resistant to individual agents; and where the combination has antimicrobial activity against microbes considered resistant to individual agents at levels appropriate for systemic administration.

Depending upon the mode of administration, the antimicrobial agent combinations and concentrations described herein can be formulated and administered using techniques known in the art. In one aspect, the antimicrobial agents described herein can be administered locally to a subject via injection. In one aspect, the antimicrobial agents can be formulated into a single composition. Thus, in this aspect, the antimicrobial agents are administered concurrently to the subject. In other aspects, each antimicrobial agent can be in separate injectable solutions (e.g., a kit composed of different vials of each antimicrobial agent to be administered). Here, the antimicrobial agents are administered sequentially to the subject.

Preparations for injectable administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

In one aspect, the antimicrobial agents can be formulated as a topical composition. For example, the antimicrobial agents can be formulated as pharmaceutically-acceptable creams, lotions, ointments, sprays, and other suitable topical formulations for localized administration. In other aspects, the antimicrobial agents can be applied to a wound dressing, where once again the administration of antimicrobial agents is localized.

In another aspect, the antimicrobial agents can be formulated into biocompatible and biodegradable packing materials or implants useful in orthopedic and dental procedures. For example, materials useful in packing joints can be formulated with the antimicrobial agents described herein in order to attain local release of the agents in the joint. Depending upon the composition of the packing material, the release pattern of the antimicrobial agents can be delayed or sustained as needed.

In other aspects, the antimicrobial agents can be formulated as instillation, solutions, irrigation solutions, or wash/soak solutions.

In a further aspect, the antimicrobial agents used herein are part of a delivery system. For example, delivery systems may provide needed solubilizing and/or separation and delivery components for the specific combination of antimicrobial agents. The delivery system can include, but are not limited to, multiple chambers, microbial filters, and sterile filtration units.

In another aspect, medical devices can be coated with the antimicrobial agents described herein. For example, medical implants (stents, catheters, artificial joints) can be coated with the antimicrobial agents described herein to prevent bacterial infection. In other aspects, surgical devices can be coated with the antimicrobial agents described herein to prevent infection during surgery.

In one aspect, described herein is a pharmaceutical composition comprising (a) at least one cephalosporin in the amount of 0.001 mg/ml to 50 mg/ml and (b) at least one polymyxin in the amount of 0.0001 mg/ml to 5 mg/ml (i.e., the first composition). In another aspect, the cephalosporin in the first composition comprises cefazolin, cefuroxime, ceftazidime, or any combination thereof in the amount of 0.001 mg/ml to 20 mg/ml (i.e., the second composition). In another aspect, the polymyxin in the second composition comprises polymyxin B in the amount of 0.0001 mg/ml to 5 mg/ml (i.e., the third composition). In another aspect, the third composition further comprises amikacin in the amount of 0.001 mg/ml to 10 mg/ml (i.e., the fourth composition). In another aspect, the fourth composition further comprises levofloxacin in the amount of 0.05 mg/ml to 10 mg/ml. In another aspect, the first to fourth compositions can be formulated as injectable solutions.

In one aspect, the pharmaceutical composition comprises (a) at least one cephalosporin in the amount of 0.001 mg/ml to 50 mg/ml and (b) at least one aminoglycoside in the amount of 0.0001 mg/ml to 20 mg/ml (i.e., the fifth composition). In another aspect, the cephalosporin and aminoglycoside in the fifth composition is cefuroxime and amikacin, respectively (i.e., the sixth composition). In another aspect, the sixth composition is cefuroxime is from 0.01 mg/ml to 20 mg/mL and the amikacin is from 0.001 mg/ml to 10 mg/ml. In another aspect, the fifth and sixth compositions can be formulated as injectable solutions.

In one aspect, described herein is a kit comprising (a) at least one cephalosporin in the amount of 0.001 mg/ml to 50 mg/ml and (b) at least one polymyxin in the amount of 0.0001 mg/ml to 5 mg/ml. In another aspect, the kit comprises (a) at least one cephalosporin in the amount of 0.001 mg/ml to 50 mg/ml and (b) at least one aminoglycoside in the amount of 0.001 mg/ml to 20 mg/ml. In another aspect, the cephalosporin, polymyxin, and aminoglycoside are each formulated as injectable solutions.

The antimicrobial agent combinations and concentrations described herein can kill a wide spectrum of bacteria quickly and effectively. Moreover, the antimicrobial agent combinations and concentrations described herein can prevent the growth of bacteria in a subject. For example, the methods and compositions described herein are effective in killing concurrently both Gram-negative bacteria and Gram-positive bacteria. Examples of Gram-negative bacteria include, but not limited to, *E. coli, Klebsiella, Enterobacter, H. influenzae, Proteus, Serratia, Pseudomonas* species, or any combination thereof. Examples of Gram-positive bacteria include, but not limited to methicillin-resistant *Staphylococcus aureus*, a staphylococcal species, or a streptococcal species. In another aspect, the bacteria can include an anaerobe such as a *Clostridium* species, a *Peptococcus* species, a *Bacteroides* species, or Mycobacteriaceae alone or in combination with Gram-positive and/or Gram-negative bacteria.

Not wishing to be bound by theory, the selection and combination of the antimicrobial agent combinations and concentrations described herein involve a combination of mechanisms of action that include, but are not limited to, the following: interference with microbial cell walls or membranes, interference with microbial DNA replication, inhibition of microbial protein synthesis, direct antimicrobial or cytotoxic effects, microbial enzyme inhibition, inhibition of microbial folic acid metabolism, interference with microbial folate metabolism, interference with microbial RNA, and interference with microbial metabolic pathways.

The antimicrobial agent combinations and concentrations described herein are effective in rapidly killing bacteria, which in turn can treat or prevent bacterial infection and the numerous symptoms associated with the infection including, but not limited to, inflammation, fever and diminished vision. Additionally, the ability to administer the antimicrobial agent combinations and concentrations described herein permit site-specific administration of the antimicrobial agents instead of systemic administration. This in turn permits the antimicrobial agents to effectively kill bacteria or prevent the growth of bacteria at a specific location in the subject. Moreover, when it is desirable or practical to only administer one to two doses of the antimicrobial agents to the subject, the use of the antimicrobial agent combinations and concentrations described herein permit this.

In one aspect, the antimicrobial agent combinations and concentrations described herein are effective in killing bacteria or preventing the growth of bacteria at or near the eye of the subject. For example, the antimicrobial agents can be administered to the eyelash area or conjunctiva, in the tear film, anterior chamber, vitreous cavity, or the subconjunctival or subtenon space. In one aspect, the antimicrobial agents are injected into a chamber of the eye of the subject. In other aspects, the antimicrobial agents can be topically applied to one or more layers of the eye or to the surface of the eye.

In other aspects, antimicrobial agents described herein can be administered to the skin or skin structures topically or by subcutaneous injection, for example, when sterility measures have been breached, placing the subject at risk of serious infection.

In another aspect, antimicrobial agents described herein can be administered in limited areas or specific organs of the body, as in implants or localized release systems, or sprays for limited dose applications.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Antibacterial Activity and Efficacy of Cefazolin, Polymyxin B, Amikacin, and/or Levofloxacin Using a Suspension Time-Kill Procedure Materials and Methods Cefazolin sodium salt, polymyxin B sulfate, amikacin (free base), and levofloxacin hydrochloride were resuspended in water and diluted for use in the study.

Efficacy of these substances, alone and in combination, was tested against two strains of bacteria using the ASTM E2315 test method.

(1) *Pseudomonas aeruginosa* 9027: This is a Gram-negative, rod-shaped microorganism with a single flagellum. *P. aeruginosa* grows optimally under aerobic conditions but can use various electron acceptors to respire anaerobically as needed. This organism is an opportunistic pathogen with the ability to form resilient biofilms in human tissues under anaerobic conditions.

(2) *Staphylococcus aureus* 33592 (MRSA): This is a Gram-positive, coccus-shaped aerobe that is resistant to methicillin, a penicillin derivative. Rapid reproduction and resistance to antibiotics can make *S. aureus* infections particularly difficult to treat. MRSA bacteria are resistant to drying and can survive on surfaces and fabrics for an extended period of time.

ASTM E2315 is a quantitative test method designed to assess changes in the populations of a microorganism in an antimicrobial liquid suspension. The method can be conducted using contact times ranging from 10 seconds to 24 hours. The test method uses non-antimicrobial agents as controls to establish baselines for microbial reductions.

The following criteria were used to establish scientific defensibility of the ASTM E2315 study:

(1) The average number of viable bacteria recovered from time zero samples must be approximately $1\times10^6$ cells/mL or greater.

(2) Ordinary consistency between replicates must be observed for the time zero samples.

(3) Positive/growth controls must demonstrate growth of the appropriate test microorganism.

(4) Negative/purity controls must demonstrate no growth of the test microorganism.

Summary of the Experimental Procedure

Test microorganisms were prepared in liquid culture medium. Suspensions of test microorganisms were standardized as needed by dilution in a buffered saline solution. Test and control substances were dispensed in identical volumes to sterile vessels.

Independently, test and control substances were inoculated with each test microorganism, then mixed and incubated. Control substances were immediately harvested and used to represent the concentration present at the start of the test.

At the conclusion of the contact time, a volume of liquid test solution was harvested and chemically neutralized. Test microorganisms were spun down and the cell pellet was resuspended in phosphate buffered saline (PBS) prior to inoculation of the test systems. 10 mL volumes of Dey/Engley neutralizer broth supplemented with 5% magnesium chloride and 35% polysorbate 80 were used for chemical neutralization. After chemical neutralization, test systems were filtered using a filtration manifold to recover surviving microorganisms.

Dilutions of neutralized test solution were assayed using appropriate growth media to determine surviving microorganism levels at each respective contact time. Reductions of microorganisms were calculated by comparing initial microbial concentrations to final microbial concentrations. The limit of detection for the assay was 10 CFU/mL.

Testing parameters used in the current study are described in Table 1.

TABLE 1

Testing Parameters

| | |
|---|---|
| Test substance volume | 5-20 mL |
| Replicates | single |
| Control substance volume | 5 mL |
| Control substance | PBS |
| Culture growth media | tryptic soy broth |
| Culture growth time | 18 hours |
| Culture dilution media | PBS |
| Inoculum volume | 20-80 µL |
| Inoculum concentration | $1.0 \times 10^6$ CFU/mL |
| Contact temperature | ambient (25° C. ± 2° C.) |
| Contact time | 2 hours |
| Volume harvested | 100 µL |
| Plating media | tryptic soy agar |
| Enumeration plate incubation temperature | 36° C. ± 1° C. |
| Enumeration plate incubation time | 24-48 hours |

Concentrations of antibiotics and identities of microorganisms used in the experimental trials are presented in Table 2.

TABLE 2

Experimental Microorganisms and Concentrations of Antibiotics

| Test Number | Test Microorganism | Antibiotic(s) and Concentration |
|---|---|---|
| 1 | *S. aureus* 33592 | Cefazolin 10 mg/mL |
| 2 | | Cefazolin 10 mg/mL |
| | | Polymyxin B 1 mg/mL |
| 3 | | Cefazolin 10 mg/mL |
| | | Polymyxin B 1 mg/mL |
| | | Levofloxacin 5 mg/mL |
| 4 | | Cefazolin 10 mg/mL |
| | | Polymyxin B 1 mg/mL |
| | | Levofloxacin 5 mg/mL |
| | | Amikacin 2 mg/mL |
| 5 | *P. aeruginosa* 9027 | Polymyxin B 1 mg/mL |
| 6 | | Polymyxin B 1 mg/mL |
| | | Cefazolin 10 mg/mL |
| 7 | | Polymyxin B 1 mg/mL |
| | | Cefazolin 10 mg/mL |
| | | Levofloxacin 5 mg/mL |

Calculations

Percent reduction of bacterial population was calculated according to the following equation, where A=number of viable test microorganisms in the test substance after the contact time and B=number of viable test microorganisms in the control substance immediately after inoculation. $Log_{10}$ reduction was also calculated.

$$\% \text{ Reduction} = \left(\frac{B-A}{B}\right) \times 100$$

$$Log_{10} \text{ reduction} = Log\left(\frac{B}{A}\right)$$

Results

Results of the study are presented in Table 3.

TABLE 3

Study Results

| Test microorganism | Contact time | Test substance | CFU/mL | % Reduction | $Log_{10}$ reduction |
|---|---|---|---|---|---|
| *S. aureus* 33592 | Time zero | Control | $2.85 \times 10^6$ | | N/A |

TABLE 3-continued

Study Results

| Test microorganism | Contact time | Test substance | CFU/mL | % Reduction | $Log_{10}$ reduction |
|---|---|---|---|---|---|
| | 2 hours | Test 1 | $1.44 \times 10^5$ | 94.96 | 1.30 |
| | | Test 2 | $1.49 \times 10^5$ | 94.77 | 1.28 |
| | | Test 3 | $1.07 \times 10^5$ | 96.25 | 1.43 |
| | | Test 4 | $4.00 \times 10^3$ | 99.86 | 2.85 |
| P. aeruginosa 9027 | Time zero | Control | $1.80 \times 10^6$ | N/A | |
| | 2 hours | Test 5 | $<1.00 \times 10^1$ | >99.9996 | >5.45 |
| | | Test 6 | $<1.00 \times 10^1$ | >99.9996 | >5.45 |
| | | Test 7 | $<1.00 \times 10^1$ | >99.9996 | >5.45 |

Although the MRSA strain used in these tests is considered to be resistant to cephalosporins, 94.96% rapid reduction of a fairly high bacterial load was observed upon exposure to cefazolin (Test 1). Thus, unexpectedly, a high concentration of a first generation cephalosporin was effective within the study contact time of two hours. Because antibiotics in this class are considered time-dependent, further reduction of bacterial populations is expected in the case of a longer contact time. While polymyxin B did not contribute further to bacterial reduction, neither was antagonism of polymyxin B and cefazolin noticed (Test 2) at this high concentration. Thus, high concentrations of these two compounds can be used in combination. Further, levofloxacin also neither enhanced nor antagonized the effects of the cefazolin/polymyxin B combination (Test 3). Finally, when amikacin (an aminoglycoside) was added, greater reductions in bacterial populations were observed, with a 99.86% kill rate (considered bactericidal). Because S. aureus 33592 is considered resistant to other aminoglycosides such as gentamicin, the added effect from amikacin in this combination (Test 4) is important. The synergistic effect of the four-antibiotic combination was demonstrated.

Meanwhile, a high concentration of polymyxin B showed essentially complete elimination of P. aeruginosa within the short two-hour time period (Test 5). Because of the efficacy of the high concentration of polymyxin B, synergistic effects of 2- and 3-drug combinations could not be observed (Tests 6 and 7). However, the additional drugs did not have antagonistic effects towards polymyxin B, showing that combinations utilizing up to these high concentrations of polymyxin B are useful.

Example 2: Antibacterial Activity and Efficacy of Cefuroxime, Amikacin, Polymyxin B, Ceftazidime, and/or Levofloxacin Using a Suspension Time-Kill Procedure The experimental procedure of Example 1 was followed with the exception of substitutions of some antibiotics. Cefuroxime (a second generation cephalosporin) and/or ceftazidime (a third generation cephalosporin active against P. aeruginosa) were used to replace cefazolin.

Concentrations of antibiotics and identities of microorganisms used in the experimental trials are presented in Table 4. Due to the strong effects of polymyxin B in Example 1, a lower concentration of this antibiotic was used in further experiments.

TABLE 4

Experimental Microorganisms and Concentrations of Antibiotics

| Test Number | Test Microorganism | Antibiotic(s) and Concentration |
|---|---|---|
| 8 | S. aureus 33592 | Cefuroxime 10 mg/mL |
| 9 | | Cefuroxime 2 mg/mL |
| | | Amikacin 2 mg/mL |
| 10 | | Cefuroxime 10 mg/mL |
| | | Amikacin 2 mg/mL |
| | | Polymyxin B 0.010 mg/mL |
| 11 | P. aeruginosa 9027 | Polymyxin B 0.010 mg/mL |
| 12 | | Cefuroxime 10 mg/mL |
| 13 | | Cefuroxime 10 mg/mL |
| | | Ceftazidime 1 mg/mL |
| 14 | | Cefuroxime 10 mg/mL |
| | | Ceftazidime 1 mg/mL |
| | | Polymyxin B 0.010 mg/mL |
| 15 | | Cefuroxime 10 mg/mL |
| | | Ceftazidime 1 mg/mL |
| | | Polymyxin B 0.010 mg/mL |
| | | Levofloxacin 5 mg/mL |

Results

Results of the study are presented in Table 5.

TABLE 5

Study Results

| Test microorganism | Contact time | Test substance | CFU/mL | % Reduction | $Log_{10}$ reduction |
|---|---|---|---|---|---|
| S. aureus 33592 | Time zero | Control | $1.75 \times 10^6$ | N/A | |
| | 2 hours | Test 8 | $1.50 \times 10^6$ | 14.29 | 0.07 |
| | | Test 9 | $3.00 \times 10^5$ | 82.86 | 0.77 |
| | | Test 10 | $1.69 \times 10^5$ | 90.34 | 1.02 |
| P. aeruginosa 9027 | Time zero | Control | $3.35 \times 10^7$ | N/A | |
| | 2 hours | Test 11 | $1.00 \times 10^3$ | 99.997 | 4.55 |
| | | Test 12 | $2.00 \times 10^5$ | 99.44 | 2.25 |
| | | Test 13 | $1.00 \times 10^1$ | 99.997 | 4.55 |

A second generation cephalosporin (cefuroxime) exhibited less activity against MRSA than the first generation cephalosporin, cefazolin, within the time frame of the present experiment (Test 8). The addition of amikacin to cefuroxime produced a substantial increase in bacterial killing, though not enough for a true bactericidal effect. However, a very high bacterial inoculum was used and thus this combination of drugs is still likely to be useful in medical applications (e.g., in prophylaxis, wound dressings) and/or clinically (Test 9). The addition of polymyxin B at a very low concentration did increase the antibacterial activity in the 2-hour experimental time frame. Previously, polymyxin B was not thought to be effective against Gram-positive bacteria and especially not against MRSA. Thus, a surprising and unexpected synergistic or additive effect of the three-drug combination has been demonstrated (Test 10). Further, this low dose of polymyxin B is expected to exhibit low or negligible toxicity.

Adding polymyxin B to cefuroxime and ceftazidime (low concentration, Test 12) and to levofloxacin (Test 13) resulted in levels of antimicrobial activity that can be considered bactericidal. Thus, the three- or four-drug combinations could be chosen for clinical use based on local toxicity parameters and individual bacterial strain susceptibility. The toxicity parameters used in these experiments are within safe limits for the anterior chamber of the eye, for example. These effects were observed even for high bacterial loads and during short time frames, previously not demonstrated.

Further, our results indicate that various concentrations of polymyxin B are effective in combination with other antibiotics; the concentration of this component of the combination can be selected based on tissue type, animal species, and/or other relevant parameters.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for killing or preventing the growth of a Staphylococcal species and a *Pseudomonas* species in an eye of a subject comprising, injecting into a chamber of the eye of the subject (a) an aminoglycoside selected from the group consisting of gentamicin, amikacin, tobramycin, debekacin, kanamvcin, neomycin, netilmicin, paromomycin, sisomycin, spectinomycin, streptomycin, or any combination thereof, (b) a polymyxin selected from the group consisting of polymyxin ft colistin, or a combination thereof, (c) at least one fluoroquinolone, and (d) a cephalosporin selected from the group consisting of cefazolin, cefuroxime, ceftazidime, or any combination thereof.

2. The method of claim 1, wherein the cephalosporin has a concentration from 0.1 mcg/ml to 50 mg/ml.

3. The method of claim 1, wherein the polymyxin has a concentration from 0.1 mcg/ml to 5 mg/ml.

4. The method of claim 1, wherein the aminoglycoside has a concentration from 0.001 mcg/ml to 20 mg/ml.

5. The method of claim 1, wherein the fluoroquinolone comprises levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, besifloxacin, or any combination thereof.

6. The method of claim 5, wherein the fluoroquinolone has a concentration from 0.01 mcg/ml to 20 mg/ml.

7. The method of claim 1, wherein the polymyxin is polymyxin B at a concentration of 0.1 mcg/ml to 5 mg/ml, the aminoglycoside is amikacin at a concentration of 0.001 mcg/ml to 20 mg/ml, the fluoroquinolone is moxifloxacin at a concentration of 0.01 mcg/ml to 20 mg/ml, and the cephalosporin is cefazolin or cefuroxime at a concentration of 0.1 mcg/ml to 50 mq/ml.

8. The method of claim 1, wherein the method further comprises administering to the eye of the subject betamethasone, dexamethasone, fludrocortisone, hydrocortisone, tixocortol, prednisolone, methylprednisolone mometasone, amcinonide, budesonide, desonide, fluocinonide, halcinonide, fluocortolone, flunisolide, fluocortolone, fluticasone, fluprednidene, beclomethasone, budesonide, clobetasone, prednicarbate, fluticasone or any combination thereof.

9. The method of claim 1, wherein the polymyxin is polymyxin B, the aminoglycoside is amikacin, the fluoroquinolone is moxifloxacin, and the cephalosporin is cefazolin or cefuroxime.

10. The method of claim 1, wherein the polymyxin is polymyxin B, the aminoglycoside is amikacin, the fluoroquinolone is levofloxacin, and the cephalosporin is cefazolin or cefuroxime.

11. The method of claim 1, wherein the polymyxin is polymyxin B in a concentration of 0.001 mg/ml to 0.1 mg/ml, the aminoglycoside is amikacin at a concentration of 0.5 mg/ml to 5 mg/ml, the fluoroquinolone is levofloxacin at a concentration of 3 mg/ml to 10 mg/ml, and the cephalosporin is cefuroxime at a concentration of 5 mg/ml to 20 mg/ml.

12. The method of claim 1, wherein the polymyxin is polymyxin B at a concentration of 0.001 mg/ml to 0.1 mg/ml, the aminoglycoside is amikacin at a concentration of 0.5 mg/ml to 5 mg/ml, the fluoroquinolone is levofloxacin at a concentration of 3 mg/ml to 10 mg/ml, and the cephalosporins are cefuroxime in the amount of 5 mg/ml to 20 mg/ml and ceftazidime at a concentration of 5 mg/ml to 20 mg/ml.

13. The method of claim 1, wherein the polymyxin is polymyxin B at a concentration of 0.5 mg/ml to 5 mg/ml, the aminoglycoside is amikacin at a concentration of 0.5 mg/ml to 5 mg/ml, the fluoroquinolone is levofloxacin at a concentration of 3 mg/ml to 10 mg/ml, and the cephalosporin is cefazolin at a concentration of 5 mg/ml to 20 mg/ml or cefuroxime in the amount of 5 mg/ml to 20 mg/ml.

14. The method of claim 1, wherein the polymyxin is polymyxin B at a concentration of 0.001 mg/ml to 0.1 mg/ml, the aminoglycoside is amikacin at a concentration of 0.5 mg/ml to 5 mg/ml, the fluoroquinolone is moxifloxacin at a concentration of 0.1 mg/ml to 0.5 mg/ml, and the cephalosporin is cefuroxime at a concentration of 5 mg/ml to 20 mg/ml.

15. The method of claim 1, wherein the polymyxin is polymyxin B at a concentration of 0.001 mg/ml to 0.1 mg/ml, the aminoglycoside is amikacin at a concentration of 0.5 mg/ml to 5 mg/ml, the fluoroquinolone is moxifloxacin at a concentration of 0.1 mg/ml to 0.5 mg/ml, and the cephalosporins are cefuroxime at a concentration of 5 mg/ml to 20 mg/ml and ceftazidime at a concentration of 5 mg/ml to 20 mg/ml.

16. The method of claim 1, wherein the polymyxin is polymyxin B at a concentration of 0.5 mg/ml to 5 mg/ml, the aminoglycoside is amikacin at a concentration of 0.5 mg/ml to 5 mg/ml, the fluoroquinolone is moxifloxacin at a concentration of 0.1 mg/ml to 0.5 mg/ml, and the cephalosporin is cefazolin at a concentration of 5 mg/ml to 20 mg/ml or cefuroxime at a concentration of 5 mg/ml to 20 mg/ml.

17. The method of claim 1, wherein the Staphylococcal species is methicillin-resistant *Staphylococcus aureus* (MRSA) and the *Pseudomonas* species is *Pseudomonas aureus*.

18. A pharmaceutical composition comprising (a) an aminoglycoside selected from the group consisting of gentamicin, amikacin, tobramycin, debekacin, kanamycin, neomycin, netilmicin, paromomycin, sisomycin, spectinomycin, and streptomycin, or any combination thereof, (b) a polymyxin selected from the group consisting of polymyxin B, colistin, or a combination thereof, (c) at least one fluoroquinolone, and (d) a cephalosporin selected from the group consisting of cefazolin, cefuroxime, ceftazidime, or any combination thereof.

19. An injectable composition comprising the composition of claim 18.

20. A medical device or delivery system comprising the composition of claim 18.

21. The composition of claim 18, wherein the polymyxin is polymyxin B at a concentration of 0.1 mcg/ml to 5 mg/ml, the aminoglycoside is amikacin is at a concentration of 0.001 mcg/ml to 20 mg/ml, the fluoroquinolone is moxifloxacin or levofloxacin at a concentration of 0.01 mcg/ml to 20 mg/ml, and the cephalosporin is cefazolin or cefuroxime at a concentration of 0.1 mcg/ml to 50 mg/ml.

22. The composition of claim 18, wherein the polymyxin is polymyxin B, the aminoglycoside is amikacin, the fluoroquinolone is moxifloxacin, and the cephalosporin is cefazolin or cefuroxime.

23. The composition of claim 18, wherein the polymyxin is polymyxin B, the aminoglycoside is amikacin, the fluoroquinolone is levofloxacin, and the cephalosporin is cefazolin or cefuroxime.

24. The composition of claim 18, wherein the polymyxin is polymyxin B, the aminoglycoside is amikacin, the fluoroquinolone is moxifloxacin or levofloxacin, and the cephalosporin is cefuroxime or cefazolin.

\* \* \* \* \*